(12) United States Patent
Miyazaki et al.

(10) Patent No.: US 7,819,643 B2
(45) Date of Patent: Oct. 26, 2010

(54) FLUID TRANSPORTATION SYSTEM WITH ELASTIC TUBE AND DETACHING CAM ARRANGEMENT

(75) Inventors: Hajime Miyazaki, Suwa (JP); Mamoru Miyasaka, Suwa (JP); Kazuo Kawasumi, Suwa (JP)

(73) Assignee: Seiko Epson Corporation (JP)

( * ) Notice: Subject to any disclaimer, the term of this patent is extended or adjusted under 35 U.S.C. 154(b) by 750 days.

(21) Appl. No.: 11/560,062

(22) Filed: Nov. 15, 2006

(65) Prior Publication Data
US 2007/0128060 A1  Jun. 7, 2007

(30) Foreign Application Priority Data
Nov. 16, 2005  (JP)  ............... 2005-331451

(51) Int. Cl.
  F04B 43/08  (2006.01)
  F04B 43/12  (2006.01)
(52) U.S. Cl. .................................. 417/477.3
(58) Field of Classification Search ................ 417/474, 417/476, 477.1, 477.3, 477.6, 477.7, 477.8, 417/479, 477.9; 74/10.31, 567, 569
  See application file for complete search history.

(56) References Cited

U.S. PATENT DOCUMENTS

| 2,297,090 A | * | 9/1942 | Weaver ......................... 74/567 |
| 2,517,142 A | * | 8/1950 | Staley .......................... 74/567 |
| 2,885,966 A | * | 5/1959 | Reginald .................. 417/477.7 |
| 3,630,647 A | * | 12/1971 | Kochlin ...................... 417/474 |
| 3,960,466 A | * | 6/1976 | Taylor ......................... 417/234 |
| 4,561,830 A | * | 12/1985 | Bradley ....................... 417/474 |
| 5,263,831 A | * | 11/1993 | Kappus .................... 417/477.7 |
| 5,488,769 A | * | 2/1996 | Natwick et al. ................ 29/888 |
| 5,575,631 A | * | 11/1996 | Jester ......................... 417/474 |
| 5,683,233 A | * | 11/1997 | Moubayed et al. .......... 417/474 |
| 6,164,921 A | * | 12/2000 | Moubayed et al. ......... 417/44.1 |
| 6,872,058 B2 | * | 3/2005 | Doig ..................... 417/477.12 |

FOREIGN PATENT DOCUMENTS

| DE | 3912310 A1 | * | 11/1989 |
| FR | 1430288 | | 4/1966 |
| GB | 2230301 | * | 10/1990 |
| JP | 2001-515557 | | 9/2001 |
| WO | WO 9116542 A1 | * | 10/1991 |

* cited by examiner

*Primary Examiner*—Devon C Kramer
*Assistant Examiner*—Nathan Zollinger
(74) *Attorney, Agent, or Firm*—Harness, Dickey & Pierce, P.L.C.

(57) ABSTRACT

A fluid transportation system includes an elastic tube, a tube frame to which the tube is attached such that the tube forms a circular arc, a first cam and a second cam disposed inside the tube, and fingers which radially extend from a rotation center in the space between the tube and the first and second cams. The first and second cams produce a first condition where the fingers are all released and a second condition where at least one of the fingers constantly closes the tube. The first and second cams sequentially press the fingers, and the fingers sequentially repeat closure and release of the tube so that fluid can continuously flow.

8 Claims, 6 Drawing Sheets

FLUID TRANSPORTATION SYSTEM WITH ELASTIC TUBE AND DETACHING CAM ARRANGEMENT

BACKGROUND

1. Field of the Invention

The present invention relates to a fluid transportation system, and more particularly to a structure of a fluid transportation system which presses an elastic tube by a plurality of fingers in accordance with rotation of cams so as to cause fluid to flow by sequentially closing and releasing the tube.

2. Background of the Invention

A known fluid transportation system (pump) has a tube disposed along a curved and concaved compressed panel and a cam disposed in the vicinity of the compressed panel and the tube. A plurality of fingers are interposed between the cam and the tube. The plural fingers, which are sequentially pressed toward the tube in accordance with the rotation of the cam, compress the tube so as to cause fluid to flow. According to this fluid transportation system, a condition where fluid is caused to flow is produced by attaching the compressed panel to a main body (for example, see Patent Reference No. 1).

[Patent Reference No. 1] JP-T-2001-515557

According to a fluid transportation system disclosed in Patent Reference No. 1, a tube is inserted into a concave of a compressed panel and the compressed panel having the tube is attached to a main body so as to bring the fluid transportation system into operable condition. Thus, complicated procedures are required before, starting operation of the system. In addition, the tube needs to be inserted into the main body in advance when the fluid transportation system is attached to other equipment or installed at a place where handling of the system is difficult.

According to this fluid transportation system, a certain number of fingers constantly close or press the tube while the tube is being attached. Thus, when the closed condition of the tube continues for a long period before operation of the fluid transportation system, the tube is permanently deformed. In this case, flow of fluid is blocked or a predetermined flow amount of fluid is not secured.

Accordingly, the invention has been developed to solve the problems discussed above. It is an object of the invention to provide a compact fluid transportation system capable of preventing permanent deformation of a tube and securing stable flow amount, producing a first condition where a plurality of fingers are all released prior to operation of the fluid transportation system and a second condition where at least one of the plural fingers constantly closes the tube after starting operation of the fluid transportation system.

SUMMARY OF THE INVENTION

A fluid transportation system according to the invention includes: an elastic tube; a tube frame having a tube guide groove to which the tube is attached such that the tube forms a circular arc; a cam driving wheel disposed inside the tube and having a rotation center coinciding with the center of the circular arc of the tube guide groove; a first cam fixed to a center shaft of the cam driving wheel; a second cam rotatably supported by the center shaft of the cam driving wheel; and a plurality of fingers which radially extend from the rotation center in the space between the tube and the first and second cams and press the tube by the rotation of the first and second cams. The first and second cams produce a first condition where the plural fingers are all released and a second condition where at least one of the plural fingers constantly closes the tube. The first and second cams sequentially press the plural fingers, and the plural fingers sequentially repeat closure and release of the tube from the inlet side to the outlet side of fluid so that fluid can continuously flow.

According to this aspect of the invention, the first condition where the plural fingers are all released and the second condition where at least one of the plural fingers constantly closes the tube are produced. By producing the first condition before operating the fluid transportation system, the condition where the fingers do not press the tube can be maintained and thus permanent deformation of the tube can be prevented. As a result, the flow amount of fluid is maintained at a predetermined value.

When the tube is attached to the tube frame under the first condition of the first cam and the second cam, no pressing load is generated by the fingers and thus assembly of the tube is facilitated.

According to the invention, it is preferable that, at a time when the fluid transportation system starts to operate, the first condition is created in a state where the second cam is attached to the first cam, and that the second condition is created in a state where the attachment between the first and second cams is released.

In this structure, the first condition is produced only through the attachment between the first cam and the second cam. Accordingly, no additional components are required to create the first condition, and thus the structure can be simplified.

According to a preferable example of this structure, when the first and second cams rotate in the first condition and the second cam comes into contact with the finger, the second cam rotates relative to the first cam in the direction opposite to the rotation direction of the first cam around the center shaft of the cam driving wheel by frictional resistance generated on a contact portion between the second cam and the finger, thereby creating the second condition by releasing attachment between the first and second cams and pressing the second cam by the first cam.

In this case, the first and second cams start rotation while being attached to each other. Then, the second cam contacts the initial finger in the rotation direction. With further rotation, the second cam gradually presses the finger and thereby the frictional resistance generated on the contact portion between the second cam and the finger increases. Since the second cam engages with the cam driving wheel with play, the second cam starts rotation relative to the first cam in the direction opposite to the rotation direction of the first cam when the frictional resistance becomes larger than the attachment force. Then, the attachment between the first cam and the second cam is released and the second condition is produced.

Accordingly, the first condition can be shifted to the second condition by starting operation of the fluid transportation system of the invention without requiring particular operation by the user.

During the period for shifting from the first condition to the second condition, the first cam performs a predetermined pressing action for the fingers so that fluid can flow in a predetermined manner, and the second cam continuously causes fluid to flow in the predetermined manner after transition to the second condition, which will be described in detail in the following preferred embodiments.

According to a preferable example of this structure, the first condition is produced by attaching the second cam to the first cam by the use of urging force given to the second cam in the thickness direction of the first cam by an elastic member provided on the second cam. The second condition is produced by removing the urging force and thus releasing the attachment between the first and second cams.

In this case, the first condition and the second condition can be produced by a simple structure without requiring additional components. When the size of the elastic member of the second cam falls within the range of the thickness of the first cam, the fluid transportation system becomes a thin device.

It is preferable that the first cam has a plurality of finger pressing portions on its outer circumference, that the second cam has at least a finger pressing portion on its outer circumference, and that the respective finger pressing portions of the first and second cams have the same pitch in the circumferential direction in the second condition.

The tube is closed when the finger pressing portions press the fingers. Since the respective finger pressing portions of the first and second cams have the same pitch in the circumferential direction, a constant flow amount of fluid can continuously flow during one rotation.

It is preferable that the plural finger pressing portions formed on the first cam and the finger pressing portion formed on the second cam have the same shape, and that an area of each finger pressing portion in the circumferential direction contacts an adjoining pair of the fingers.

It is preferable that two of the fingers close the tube and a condition where one of the fingers closes the tube are alternately repeated.

In this structure, the fingers pressed by the finger pressing portions can be sequentially switched during the rotation of the first and second cams. By arranging the structure such that two fingers can simultaneously contact each finger pressing portion, the tube is constantly closed by one of the fingers being pressed during the period for switching the fingers to be pressed. It is therefore possible to prevent reverse flow of fluid and cause fluid to flow continuously.

The fluid transportation system is characterized in that loading torque of the cam driving wheel is kept substantially constant for one rotation of the cam driving wheel during operation of the fluid transportation system.

For example, a step motor can be used as the driving source.

According to this structure, since variation in the loading torque is reduced, the safety factor of the rotational torque of the driving source is decreased. As a result, the driving source can be made compact and variation in the flow amount of fluid can be reduced.

It is preferable that the tube and the plural fingers can be inserted into the tube frame in the same direction.

In this case, assembly of the tube and the fingers can be facilitated. Since the tube and the fingers are attached with the first and second cams under the first condition, the fluid transportation system is easily assembled even when the system is a small device.

It is preferable that a tube guide having a slope for returning the tube to an initial position prior to closure of the tube at the time of shifting from the condition where the tube is closed by the fingers to the condition where the closure is released is provided on the bottom of the tube guide groove.

Since the tube guide securely returns the closed and deformed tube to the position of the initial condition, stable flow of fluid can be maintained.

Moreover, this function can be provided by a simple structure without requiring additional components.

DETAILED DESCRIPTION OF THE PREFERRED EMBODIMENTS

A preferred embodiment according to the invention is hereinafter described with reference to the drawings.

FIGS. 1 through 9 illustrate a fluid transportation system in an embodiment according to the invention. FIGS. 1 through 4 are a plan view and cross-sectional views of the fluid transportation system. FIGS. 5 through 9 are plan views and cross-sectional views showing conditions of the fluid transportation system during operation.

Figure 1:
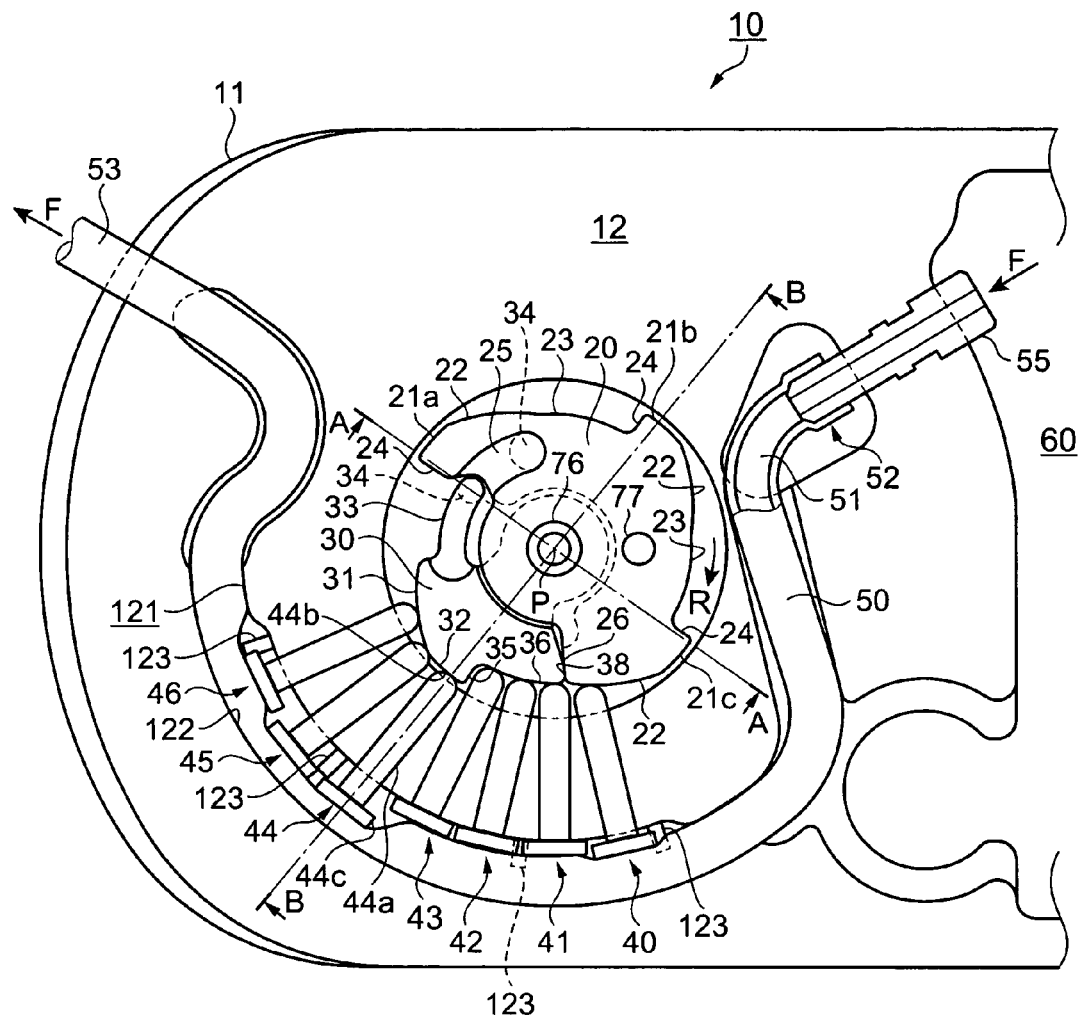
FIG. 1 is a plan view showing a fluid transportation mechanism of a fluid transportation system in an embodiment according to the invention.
Figure 2:
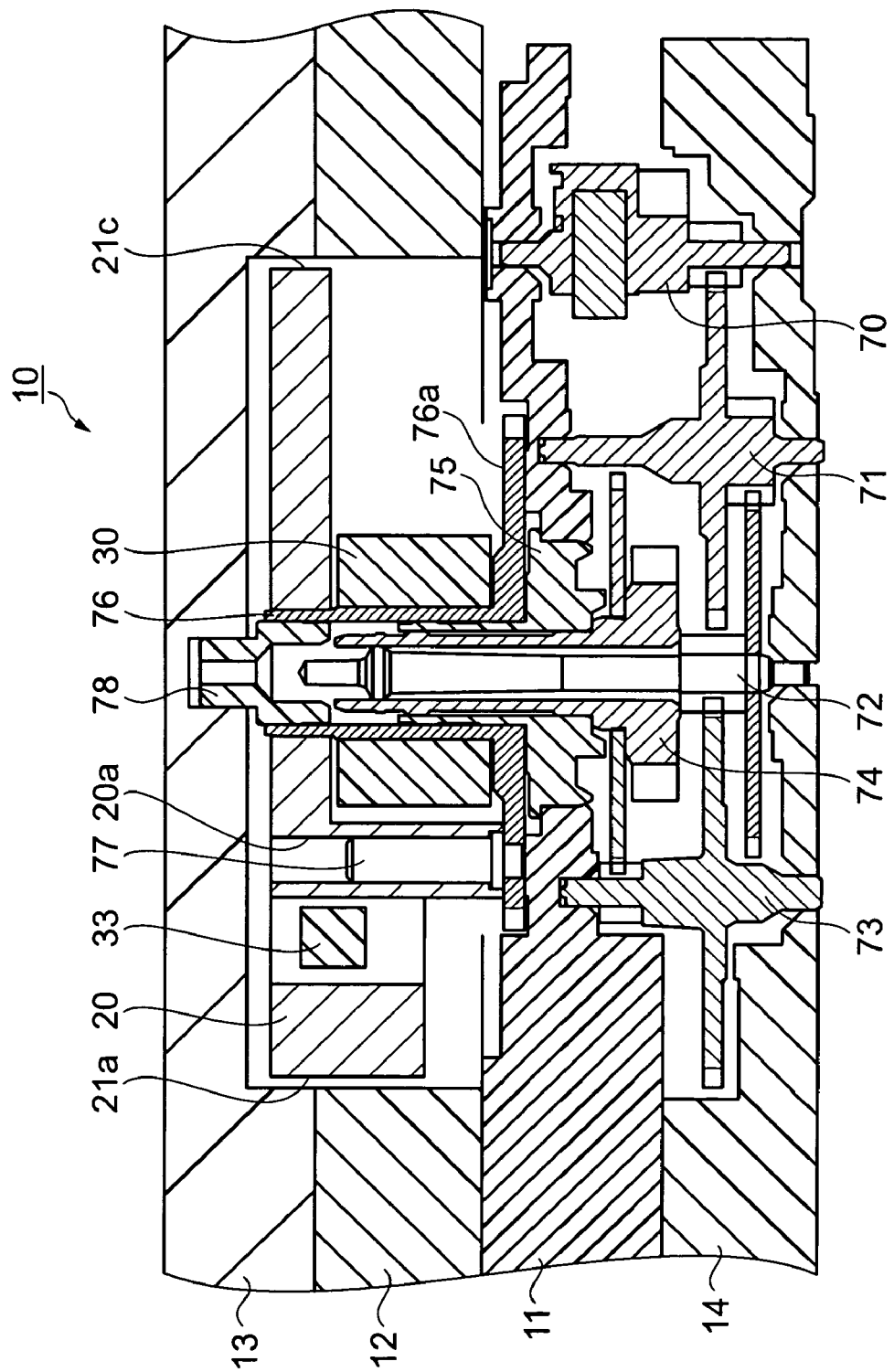
FIG. 2 is a partial cross-sectional view taken along a line A-A in FIG. 1.
Figure 3:
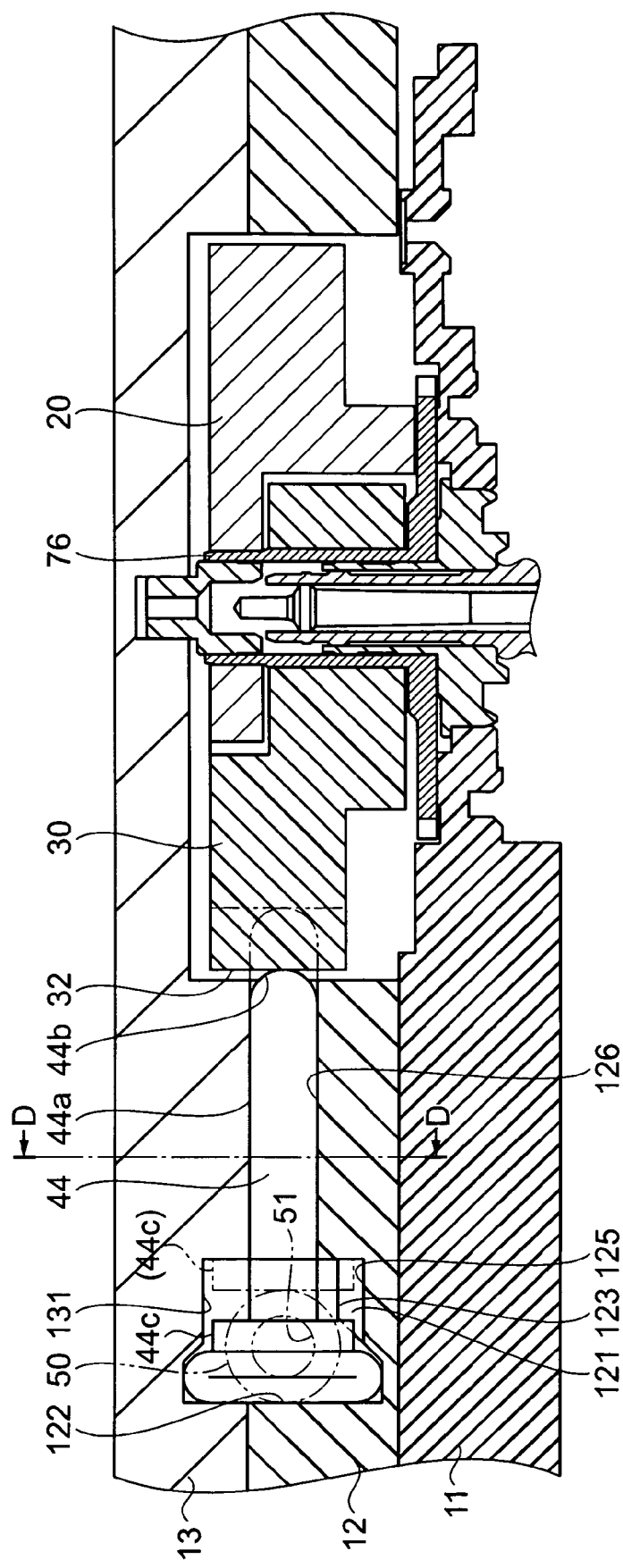
FIG. 3 is a partial cross-sectional view taken along a line B-B in FIG. 1.
Figure 4:
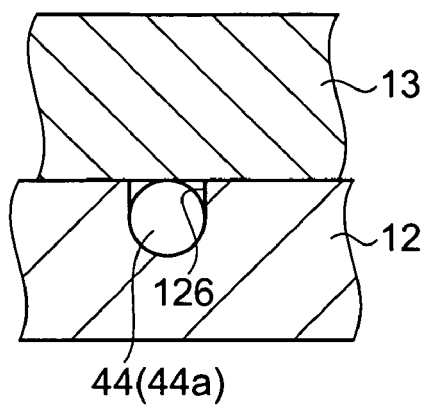
FIG. 4 is a cross-sectional view taken along a line D-D in FIG. 3.

FIG. 1 is a plan view illustrating a part of the fluid transportation system in the embodiment. FIG. 2 is a partial cross-sectional view taken along a line A-A in FIG. 1. FIG. 3 is a partial cross-sectional view taken along a line B-B in FIG. 1. FIG. 4 is a cross-sectional view taken along a line D-D in FIG. 3. FIGS. 1 through 4 show a state in a second condition where a fluid transportation system 10 normally operates.

A structure of the fluid transportation system 10 in this embodiment is now described with reference to FIGS. 1 and 2. As illustrated in FIGS. 1 and 2, the fluid transportation system 10 in this embodiment basically includes a driving transmission unit for transmitting driving force to a fluid transportation mechanism, a tube 50 in which fluid flows, the fluid transportation mechanism which rotates a first cam 20 and a second cam 30 by the driving force transmitted from the driving transmission unit and sequentially closes the tube 50 from the fluid inlet side to the outlet side so that fluid can flow, and a fluid storage unit 60 for storing fluid.

Initially, the structure of the driving transmission unit is discussed with reference to FIG. 2. FIG. 2 is a partial cross-sectional view taken along a line A-A in FIG. 1. As illustrated in FIG. 2, the driving transmission unit has a step motor (not shown) as the driving source, and transmits rotation of a step rotor 70 of the step motor to a cam driving wheel 76 through the sequential tooth-engagement of a first transmission wheel 71, a second transmission wheel 72, a third transmission wheel 73, and a fourth transmission wheel 74.

The step rotor 70, the first transmission wheel 71, the third transmission wheel 73, and the fourth transmission wheel 74 are rotatably supported by a first frame 11 and a second frame 14. A transmission wheel shaft 75 is inserted into the first frame 11, and the cylindrical portion of the transmission wheel shaft 75 projects upward (toward the positions of the first cam 20 and the second cam 30). The cylindrical portion of the fourth transmission wheel 74 is inserted through a through hole formed on the transmission wheel shaft 75, and the shaft portion of the second transmission wheel 72 is inserted through a through hole formed on the fourth transmission wheel 74.

One supporting shaft of the second transmission wheel 72 is supported by the second frame 14, and the other supporting shaft is supported by the through hole of the fourth transmission wheel 74. The rotation of the fourth transmission wheel 74 is transmitted to the cam driving wheel 76 via a not-shown fifth transmission wheel.

The cam transmission wheel 76 is supported by the transmission wheel shaft 75 by the engagement between a through hole formed at the center of the cam driving wheel 76 and the outer circumference of the cylindrical portion of the transmission wheel shaft 75. The shaft portion of the cam driving wheel 76 projects toward the positions of the first cam 20 and the second cam 30. The upper part of the shaft portion of the cam driving wheel 76 is supported by a cam driving wheel support bearing 78 inserted into a lid 13. The lid 13 has a hole on which the cam driving wheel supporting bearing 78 is supported. This hole does not penetrate through the lid 13, and the end of the cam driving wheel supporting bearing 78 is sealed by the lid 13. The cam driving wheel 76 receives the rotation of the step rotor 70 whose rotation speed is decreased to a predetermined speed by the above respective transmission wheels.

Since the cam driving wheel 76 is supported by the transmission wheel shaft 75 and the cam driving wheel supporting bearing 78, the degree of inclination of the cam driving wheel 76 having a short length between the supporting points is reduced. Thus, side pressure produced by loading torque of the first cam 20 and the second cam 30, which torque will be described later, and applied to the shaft portion of the cam driving wheel 76 is decreased.

The structure of the fluid transportation mechanism in the cross-sectional view is now explained with reference to FIG. 2. The fluid transportation mechanism is disposed on the upper surface side of the first frame 11 above the driving transmission unit. The second cam 30 and the first cam 20 are attached to the projecting shaft portion of the cam driving wheel 76 in this order from the lower position. The second cam 30 is supported by the cam driving wheel 76 through the engagement therewith leaving play. The first cam 20 is fixed to the cam driving wheel 76 in such a manner as to rotate with the cam driving wheel 76 as one piece.

A rotation stop shaft 77 is inserted into a flange 76a of the cam driving wheel 76, and the projecting shaft portion of the rotation stop shaft 77 is inserted into a hole 20a formed on the first cam 20. The rotation stop shaft 77 is positioned away from the cam driving wheel 76 (see FIG. 1 for the position in the plan view). The rotation stop shaft 77 reinforces the rotation of the first cam 20 so as to prevent idle running of the first cam 20 with respect to the cam driving wheel 76.

FIGS. 1 and 2 illustrate a state where the first cam 20 and the second cam 30 are in a second condition. In this condition, a spring 33 provided on the second cam 30 is released, and the clearance between the end of the spring 33 (friction engaging portion 34) and the first cam 20 in the circumferential direction is established as the minimum distance for releasing the engagement between the end of the spring 33 (friction engaging portion 34) and the first cam 20 so that the pitch of a finger pressing portion 32 of the second cam 30 can be maintained equal to the pitch of finger pressing portions of the first cam 20 even when the second cam 30 starts rotation before initiation of rotation of the first cam 20 due to shock or other reasons.

A tube frame 12 is provided around the first cam 20 and the second cam 30. The tube frame 12 is held between the lid 13 and the first frame 11. The lid 13, the tube frame 12, and the first frame 11 are superposed with and attached to each other by a not-shown screw. The first frame 11 and the second frame 14 are also superposed with and attached to each other by a not-shown screw. The respective contacting surfaces are brought into tight contact with one another.

Next, the fluid transportation mechanism in this embodiment is discussed with reference to FIG. 1.

FIG. 1 is a plan view showing a part of the fluid transportation system 10 in this embodiment. FIG. 1 illustrates a condition where the fluid transportation system 10 operates in a steady state, which is viewed through the lid 13. As illustrated in FIG. 1, the fluid transportation mechanism in this embodiment includes the first cam 20 and the second cam 30 attached to or supported by the cam driving wheel 76, the tube 50 in which fluid flows, and seven fingers 40 through 46 interposed between the tube 50 and the first and second cams 20 and 30 and radially extending from a rotation center P of the cam driving wheel 76. The respective fingers 40 through 46 are disposed at equal intervals.

The center of the first cam 20 is fixed to the shaft portion of the cam driving wheel 76. The first cam 20 has three projecting portions on its outer circumference, and forms a finger pressing unit on its outermost circumference. The finger pressing unit is constituted by three finger pressing portions 21a through 21c. The finger pressing portions 21a through 21c are formed on a concentric circle at an equal distance away from the rotation center P. The pitch in the circumferential direction and the external shape of the finger pressing portion 21a are the same as those of the finger pressing portion 21b, and the pitch in the circumferential direction and the external shape of the finger pressing portion 21b are the same as those of the finger pressing portion 21c. The distance between the finger pressing portion 21a and the finger pressing portion 21c is twice larger than each of the pitch in the circumferential direction between the finger pressing portions 21a and 21b and the pitch in the circumferential direction between the finger pressing portions 21b and 21c.

A concave is formed at the base of the finger pressing portion 21a on a concentric circle of the rotation center P of the cam driving wheel 76 (in coincidence with the rotation center of the first cam 20 and the second cam 30). A second cam carrying surface 25 on which the spring 33 of the second cam 30 rides as will be described later is formed on the bottom of the concave. Each of the finger pressing portions 21a through 21c is formed continuously from a finger pressing slope 22 and a circular-arc portion 23 on a concentric circle around the rotation center P. The circular arc 23 is positioned away from the fingers 40 through 46 so as not to press the fingers 40 through 46.

One end of each of the finger pressing portions 21a, 21b and 21c is connected with the circular-arc portion 23 by a linear portion 24 on an extension line from the rotation center P. The second cam 30 is supported by the shaft portion of the cam driving wheel 76 below the first cam 20. The second cam 30 is rotatably attached to the shaft portion of the cam driving wheel 76.

The second cam 30 has the finger pressing portion 32 having the same shape as the shapes of the finger pressing portions 21a, 21b and 21c of the first cam 20, and a finger pressing slope 31 having the same shape as the shape of the finger pressing slope 22. The second cam 30 has the spring 33 as an elastic member projecting in the shape of peninsula. The spring 33 is disposed on the concentric circle around the rotation center P, and is so shaped as to be accommodated within the concave (second cam carrying surface 25) formed on the first cam 20 discussed above. The cylindrical friction engaging portion 34 projects from the back surface of the end of the spring 33.

The second cam 30 has a circular-arc portion 36 having the same radius as that of the circular-arc portion 23 of the first cam 20 in the direction opposite to the spring 33 in the plan view, and a linear portion 35 connecting the circular-arc portion 36 and the finger pressing portion 32 on an extension line from the rotation center P.

The relative structures of the first cam 20 and the second cam 30 are now explained. Since the first cam 20 is fixed to the shaft portion of the cam driving wheel 76, the first cam 20 rotates with the cam driving wheel 76 in the direction of an arrow R. On the other hand, since the second cam 30 engages with the shaft portion of the cam driving wheel 76 with play, the second cam 30 does not follow the rotation of the first cam 20. However, when a first cam engaging portion 38 formed at the end of the second cam 30 engages with a second cam engaging portion 26 at the end of the finger pressing portion 21c of the first cam 20, the rotational force of the first cam 20 is transmitted from the second engaging portion 26 to the first cam engaging portion 38. As a result, the second cam 30 starts rotation with the first cam 20 and thus comes to a condition for pressing the fingers 40 through 46. This condition is referred to as the second condition.

In the second condition, the engagement between the spring 33 of the second cam 30 and the second cam carrying surface 25 of the first cam 20 is released, and thus the first cam 20 and the second cam 30 form a cam having the finger pressing portions 21a through 21c and 32 at four positions.

Though not shown in the figure, the finger pressing portions 21a through 21c and 32 are formed on a concentric circle around the rotation center P, and each of the finger pressing portions has such a length that an adjoining pair of the fingers can contact a finger pressing area formed by the concentric circle.

The tube 50 in which fluid flows is disposed at a position away from the first cam 20 and the second cam 30. The tube 50 is an elastic component made of silicone rubber in this embodiment. The tube 50 is inserted into a tube guide groove 121 formed on the tube frame 12. An outlet 53 through which fluid is discharged to the outside is provided at one end of the tube 50 and projects to the outside of the fluid transportation system 10. An inlet 52 through which fluid enters is provided at the other end of the tube 50 and connected with a connection pipe 55. An end of the connection pipe 55 communicates with the fluid storage unit 60 (not shown) for storing fluid.

The tube 50 is inserted into the tube guide groove 121 formed in such a position that the range of the tube 50 pressed by the fingers 40 through 46 lies on a concentric circle around the rotation center P. The fingers 40 through 46 are interposed between the tube 50 and the first and second cams 20 and 30 and radially extend from the rotation center P.

Since the fingers 40 through 46 have the same shape, the finger 44 is now discussed as an example. The finger 44 is constituted by a cylindrical shaft portion 44a, a flange 44c provided at one end of the shaft portion 44a, and a contact portion 44b provided at the other and having a semi-spherical shape. The flange 44c is a pressing portion for pressing the tube 50, and the contact portion 44b is a pressed portion to be pressed by the first cam 20 or the second cam 30. The fingers 40 through 46 are inserted into finger guide grooves 126 formed on the tube frame 12, and the respective directions of the cross sections of the fingers 40 through 46 are maintained by the lid 13 (see FIG. 4).

The fingers 40 through 46 reciprocate along the finger guide grooves 126. The fingers 40 through 46 pressed toward outside by the first cam 20 and the second cam 30 press the tube 50 against a tube guide wall 122 of the tube guide groove 121 to close a fluid flow area 51 (see FIG. 3 as well). The centers of the cross sections of the fingers 40 through 46 are substantially in coincidence with the center of the tube 50.

The fluid transportation mechanism in this embodiment has the structure described above. FIG. 1 illustrates a state in the second condition where fluid is transported.

Next, the operation performed for transportation of fluid in this embodiment is described with reference to FIG. 1. FIG. 1 shows a state in the second condition. The finger pressing portion 32 of the second cam 30 presses the finger 44 and the finger 45 contacts the joint between the finger pressing portion 32 and the finger pressing slope 31 to close the tube 50. The finger 46 positioned on the finger pressing slope 31 presses the tube 50 but does not perfectly close the tube 50 since the degree of pressing by the finger 46 is smaller than that by the finger 44.

The fingers 41 through 43 are located within the range of the circular-arc portion 36 of the second cam 30, and thus are not pressed at the initial position. The finger 40 contacts the finger pressing slope 22 of the first cam 20, but still does not close the tube 50 at that position.

When the first cam 20 and the second cam 30 rotate in the direction of the arrow R from this position, the finger pressing portion 32 of the second cam 30 presses the fingers 45 and 46 in this order and closes the tube 50. The finger 44 is separated from the finger pressing portion 32 and releases the tube 50. Fluid flows into the fluid flow area 51 at positions where the fingers release the tube 50 from closure or the fingers do not yet close the tube 50.

When the first cam 20 further rotates, the finger pressing slope 22 sequentially presses the fingers 40, 41, 42 and 43 in this order, and closes the tube 50 when the finger pressing portion 21c reaches the fingers.

By repeating these processes, fluid is caused to flow from the inlet 52 toward the outlet 53, and then is discharged through the outlet 53 (in the direction of an arrow F).

In this step, each of the finger pressing portions of the first cam 20 and the second cam 30 contacts two of the fingers, and presses one of the fingers when shifting to the position for pressing the next finger. By repeating two-finger pressing and one-finger pressing, the condition where at least one finger constantly closes the tube 50 is produced. Thus, when the first cam 20 and the second cam 30 sequentially press the fingers, one of the fingers is constantly pressed to close the tube 50 even when the fingers being pressed are changed. It is therefore possible to prevent reverse flow of fluid and cause fluid to continuously flow.

The detailed structure for closing the tube 50 by the fingers is now described with reference to the figures. A condition where the finger 44 closes the tube 50 is discussed as an example.

FIG. 3 is a partial cross-sectional view taken along a line B-B in FIG. 1. FIG. 4 is a partial cross-sectional view taken along a line D-D in FIG. 3. As illustrated in FIG. 3, a major part of the tube 50 in the cross-sectional direction is inserted into the tube guide groove 121 formed on the tube frame 12, and held at a position shown in FIG. 3 (shown by an alternate long and two short dashes line in the figure).

The finger 44 is inserted into the finger guide groove 126 formed on the tube frame 12 (see FIG. 4). A concave 125 in which the flange 44c of the finger 44 is movable is formed at the connection between the finger guide groove 126 and the tube guide groove 121. A concave is further formed in the lower region of the tube guide wall 122 extending in the vertical direction from the tube guide groove 121. This concave provides a sufficient space for the tube 50 after deformed by closure.

The lid 13 is placed above the tube 50. The lid 13 has a groove at a position corresponding to the tube guide groove 121 in a size sufficient for accommodating the tube 50, a concave 131 corresponding to the concave 125, and a concave as a sufficient space for the tube 50 after deformed by closure. The fluid flow area 51 of the tube 50 is not closed when the tube pressing portion of the first cam 20 or the second cam 30 does not press the fingers (the position of the finger 44 in this condition is shown by an alternate long and two short dashes line).

FIG. 3 shows a condition where the second cam 30 presses the finger 44. The finger 44 pressed by the finger pressing portion 32 closes the tube 50. When the finger 44 retreats and releases the closure of the tube 50, the shape of the fluid flow area 51 returns to the original shape. In this step, the tube 50 securely returns to the initial position (position shown by an alternate long and two short dashes line) by a tube guide portion 123 as a partially projecting part of the concave 125 of the tube frame 12.

The tube guide portion 123 has a slope in the direction of the tube 50 to assist the tube 50 to return to the initial position. As illustrated in FIG. 1, the tube guide portion 123 is provided at four positions which are near the outer side of the finger 40, between the fingers 41 and 42, between the fingers 44 and 45, and near the outer side of the finger 46. These tube guide portions 123 urge the tube 50 to securely return from the closure position to the release position.

Next, the assembly method of the fingers 40 through 46 and the tube 50 are explained. The fingers (finger 44 is shown as an example) are inserted into the finger guide grooves 126 formed on the tube frame 12 from above (see FIG. 4). Then, the tube 50 is inserted into the tube guide groove 121, and the lid 13 is placed for completing the assembly. During assembly, the first cam 20 and the second cam 30 are at the positions in the first condition shown in FIG. 5. In the first condition which will be described later in detail, neither the first cam 20 nor the second cam 30 presses the fingers 40 through 46. Thus, no load is applied to the tube 50 and the fingers 40 through 46, which facilitates the assembly procedures.

The assembly order of the fingers 40 through 46 and the tube 50 may be switched.

Next, the method of shifting from the first condition immediately before the operation start to the second condition as the steady-state operation condition of the fluid transportation system 10 in this embodiment is discussed with reference to the figures.

Figure 5:
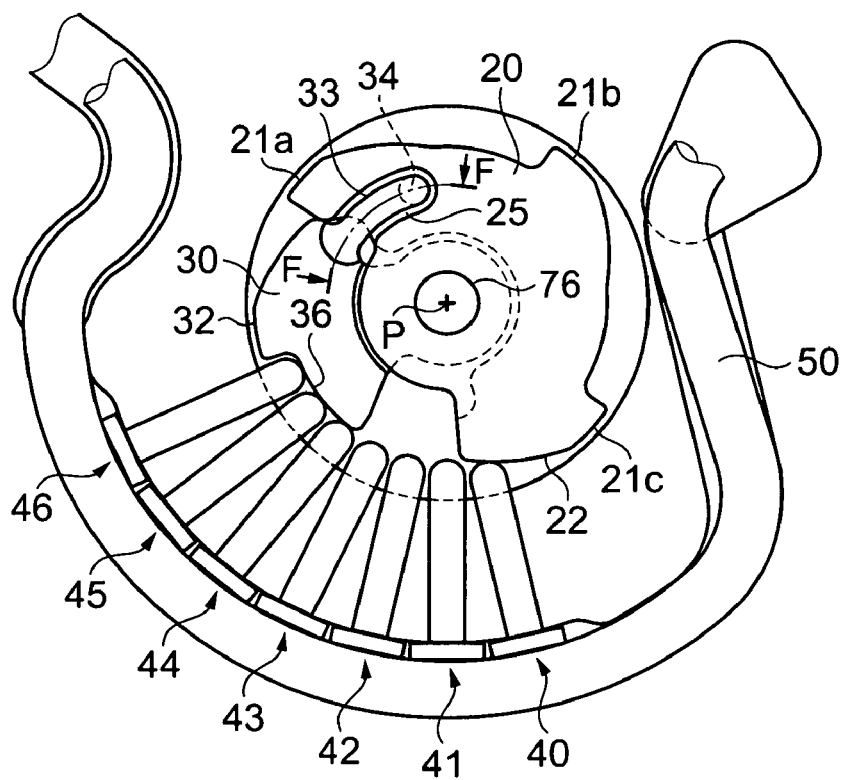
FIG. 5 illustrates a first condition of the fluid transportation system in the embodiment according to the invention.

FIG. 5 shows the first condition of the fluid transportation system 10. This condition also corresponds to a state immediately after assembly of the fluid transportation system 10. The first cam 20 and the second cam 30 are assembled such that the spring 33 of the second cam 30 is disposed on the second cam carrying surface 25 of the first cam 20. More specifically, the first condition is produced by slightly bending the spring 33 of the second cam 30 upward and placing the spring 33 on the second cam carrying surface 25 shown in the figure.

Figure 6:
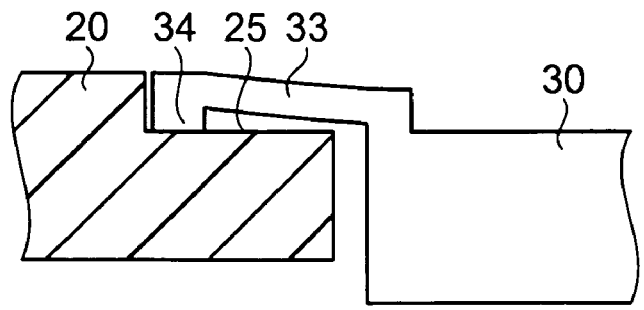
FIG. 6 is a cross-sectional view taken along a line F-F in FIG. 5.

The condition produced in this step is shown in FIG. 6.

FIG. 6 is a cross-sectional view taken along a line F-F in FIG. 5. As illustrated in FIG. 6, the spring 33 of the second cam 30 rides on the second cam carrying surface 25. The friction engaging portion 34 projecting from the end of the spring 33 is urged against the second cam carrying surface 25 by the elastic force of the spring 33 in the upward and downward direction (thickness direction). The second cam 30 is attached and held by the first cam 20 by this elastic force, and this condition is maintained until the fluid transportation system 10 starts operation. The friction engaging portion 34 is provided to maintain the current state in the first condition, and decrease frictional resistance during the period for shifting to the second condition.

The depth of the second cam carrying surface 25 from its upper surface is preferably established such that the upper surface of the spring 33 of the second cam does not project from the upper surface of the first cam 20 in the condition shown in FIG. 6.

The relative positions of the first cam 20 and the second cam 30 are now discussed with reference to FIG. 5. As illustrated in FIG. 5, the first cam 20 and the second cam 30 are positioned in the plan view such that the fingers 40 through 46 are disposed between the finger pressing portion 21c of the first cam 20 and the finger pressing portion 32 of the second cam 30. Thus, the finger 40 contacts a part of the finger pressing slope 22, but at this position the finger 40 does not press the tube 50.

The fingers 41, 42 and 43 are positioned in an area where neither the first cam 20 nor the second cam 30 is present. The fingers 44, 45 and 46 are positioned within the area of the circular-arc portion 36 of the second cam 30, and thus do not press the tube 50. Thus, the fingers 40 through 46 and the tube 50 can be attached in the same direction with no interference caused among the first cam 20, the second cam 30, the fingers 40 through 46, and the tube 50 when the fluid transportation system 10 (fluid transportation mechanism) is assembled in the first condition.

Moreover, the fluid flow area 51 of the tube 50 is kept released while the first condition discussed above is being maintained. Thus, deformation of the tube 50 is prevented.

Next, the processes performed when shifting from the first condition to the second condition are explained with reference to the figures.

Figure 7:
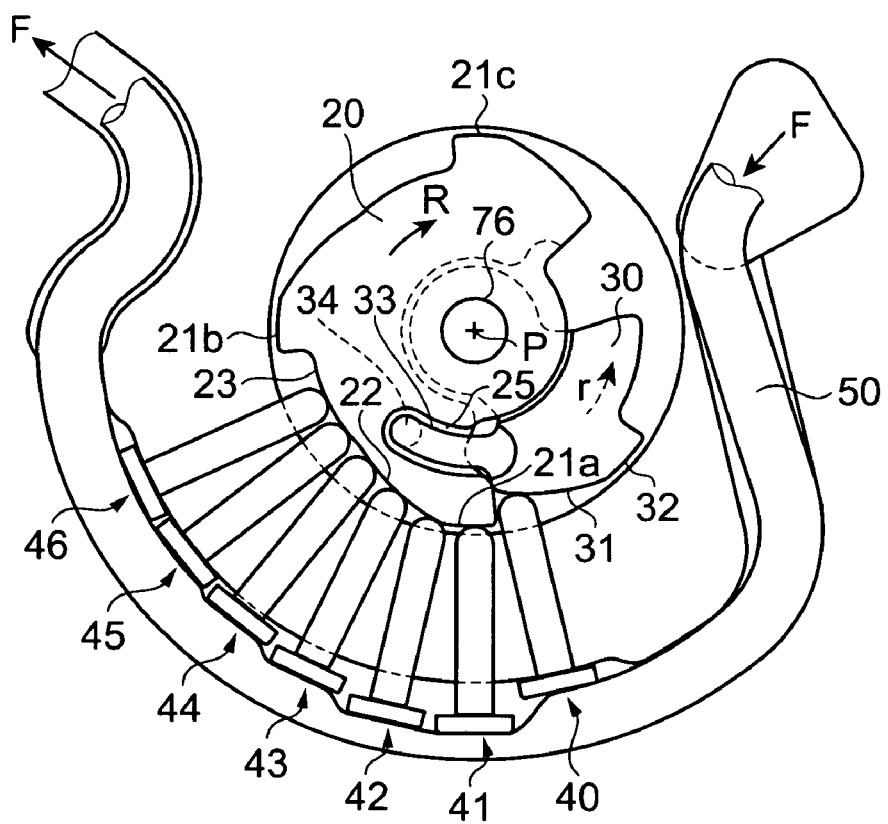
FIG. 7 illustrates an initial condition in a transition period from the first condition to a second condition after the fluid transportation system starts operation.

FIG. 7 shows an initial condition at the time of shifting from the first condition to the second condition after the fluid transportation system 10 starts operation. As illustrated in FIG. 7, the first cam 20 and the second com 30 in the condition shown in FIGS. 5 and 6 rotate in the direction of the arrow R. The second cam 30 and the first cam 20 in the condition of FIG. 5 rotate while attached to each other. In this step, the finger pressing portions 21c, 21b and 21a of the first cam 20 sequentially press the fingers 40 through 46 so as to cause fluid to flow.

When the finger pressing slope 31 of the second cam 30 comes into contact with the finger 40, the shifting period to the second condition starts. When the finger pressing slope 31 reaches the finger 40 and the first cam 20 further rotates in the direction of the arrow R, the finger pressing slope 31 gradually presses the finger 40 and the finger 40 starts pressing the tube 50. Thus, frictional resistance generated between the finger pressing portion 32 and the finger 40 increases.

The second cam 30 engages with the cam driving wheel 76 with play, and the relative positions of the second cam 30 and the first cam 20 are maintained only by frictional resistance generated between the spring 33 and the second cam carrying surface 25. Thus, the second cam 30 begins to rotate in the direction of an arrow r relative to the second cam 30 when the frictional resistance between the finger pressing slope 31 and the finger 40 becomes larger than the frictional resistance between the spring 33 and the second cam carrying surface 25.

Figure 8:
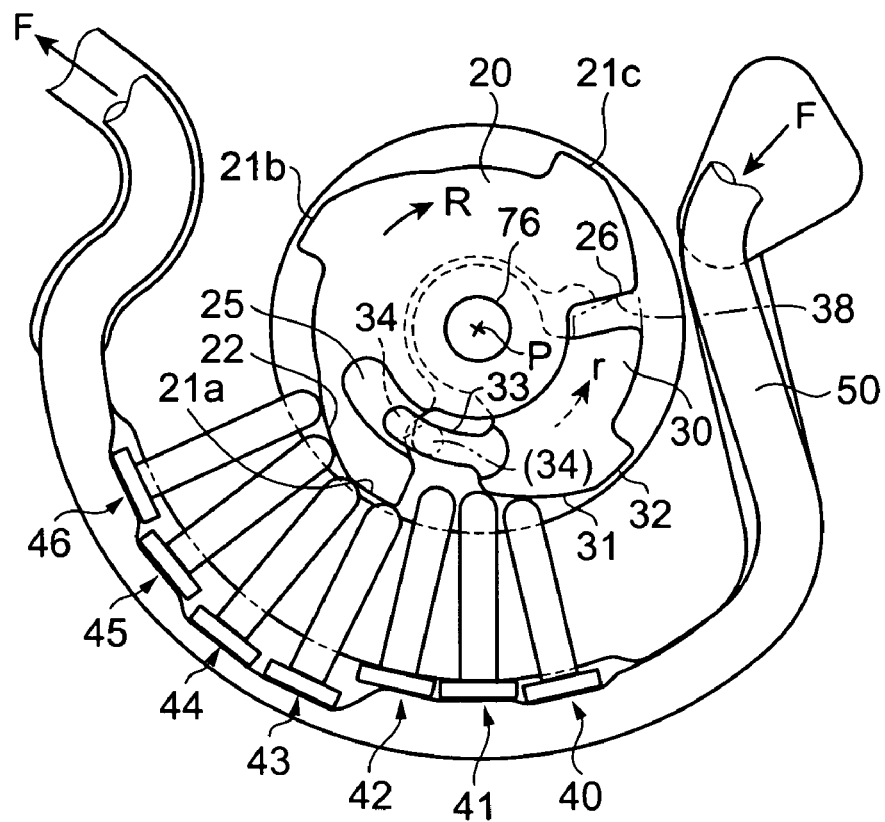
FIG. 8 illustrates a condition when a first cam further rotates from the condition shown in FIG. 7.

Then, the relative positions of the first cam 20 and the second cam 30 shift as illustrated in FIG. 8.

FIG. 8 shows a condition where the first cam 20 further rotates in the direction of the arrow R from the condition of FIG. 7. As illustrated in FIG. 8, the first cam 20 rotates and reaches a position where the finger pressing portion 21a presses the fingers 43 and 44. In this step, the second cam 30 follows the rotation of the first cam 20. The fingers 40 and 41 ride on the finger pressing slope 31. The sum of the frictional resistances between the finger pressing portion 32 and the finger 40 and between the finger pressing portion 32 and the finger 41 gradually increases to be larger than the frictional resistance between the spring 33 and the second cam carrying surface 25, and the second cam 30 begins to rotate in the direction of the arrow r relative to the first cam 20. Then, the spring 33 disengages from the second cam carrying surface 25 (condition shown by an alternate long and two short dashes line in the figure), and the attached condition of the first cam 20 and the second cam 30 is separated.

Figure 9:
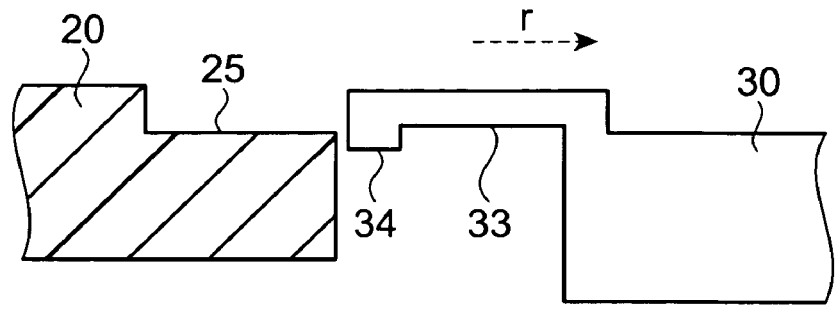
FIG. 9 is a partial cross-sectional view of the condition shown in FIG. 8.

This condition is shown in the cross-sectional view of FIG. 9. The spring 33 of the second cam 30 disengages from the second cam carrying surface 25 and returns to the initial condition by its own elastic force.

When the first cam 20 further rotates in the direction of the arrow R, the first cam engaging portion 38 of the second cam 30 comes into contact with the second cam engaging portion 26 of the first cam 20 and the second cam 30 is rotated in the direction of the arrow R by the first cam 20. As a result, the second condition shown in FIG. 1 is produced. In this condition, the first cam 20 and the second cam 30 become a cam having the finger pressing portions with the same pitch and the same shape. The respective finger pressing portions 21a, 21b, 21c and 32 press and release the fingers 40 through 46, and thus the fingers 40 through 46 sequentially repeat closure and release of the tube 50 in the direction from the inlet 52 to the outlet 53 so that fluid can continuously flow.

The loading torque (rotational torque) of the cam driving wheel 76 at the time of continuous rotation in the second condition is kept substantially constant during one rotation of the cam driving wheel 76 (first cam 20 and second cam 30). This is explained referring to the conditions shown in FIGS. 7 and 8.

The loading torque of the cam driving wheel 76 in the condition of FIG. 7 is represented by the sum of the loading torque for pressing the finger 41 by the finger pressing portion 21a of the firs cam 20, the loading torque for pressing the fingers 42, 43 and 44 by the finger pressing slope 22, and the loading torque for pressing the finger 40 by the finger pressing slope 31 of the second cam 30. The loading torque for the fingers 45 and 46 can be ignored since they are located in the range of the circular-arc portion 23.

The loading torque of the cam driving wheel 76 in the condition of FIG. 8 is represented by the sum of the loading torque for pressing the fingers 43 and 44 by the finger pressing portion 21a of the firs cam 20, the loading torque for pressing the fingers 45 and 46 by the finger pressing slope 22, and the loading torque for pressing the finger 40 by the finger pressing slope 31 of the second cam 30. The loading torque for the fingers 41 and 42 can be ignored.

Since the respective finger pressing portions of the first cam 20 and the second cam 30 have the same pitch and shape in the second condition and the respective fingers are disposed at equal intervals, the loading torque in the condition of FIG. 7 and the loading torque in the condition of FIG. 8 are substantially constant. The loading toque during one rotation is not greatly variable but kept substantially constant at any positions other than the positions shown in FIGS. 7 and 8.

In this embodiment, therefore, the first condition where all the fingers 40 through 46 are released and the second condition where at least one of the fingers 40 through 46 constantly closes the tube are created. By creating the first condition before operating the fluid transportation system 10 (maintaining the system in the assembly condition), the condition where the fingers 40 through 46 do not press the tube 50 can be maintained and thus deformation of the tube 50 can be prevented. As a result, the flow amount of fluid is maintained at a predetermined value.

When the tube 50 and the fingers 40 through 46 are attached to the tube frame under the first condition of the first cam 20 and the second cam 30, no pressing load is generated and thus assembly of the tube 50 and the fingers 40 through 46 is facilitated.

The first condition is produced by urging and attaching the second com 30 to the first cam 20 in the thickness direction by utilizing the elastic force of the spring 33 provided on the second cam 30 at the operation start of the fluid transportation system 10 (condition at assembly), and the second condition is produced by releasing the attachment between the first cam 20 and the spring 33. Thus, only a simple structure is required for producing the first condition without using additional component.

When the operation starts in the first condition, the finger pressing slope 31 of the second cam 30 contacts the finger 40. With further rotation, the second cam 30 gradually presses the finger 40, and thus the frictional resistance generated on the contact area between the second cam 30 and the finger 40 increases. The attachment is separated when the frictional resistance becomes larger than the attachment force, thereby creating the second condition. Thus, the first condition can be shifted to the second condition without requiring operation by the user.

During the transition period from the first condition to the second condition, a predetermined amount of fluid is caused to flow by the fingers executing the predetermined pressing action in accordance with the movement of the first cam 20. After the transition to the second condition is completed, the predetermined flow continues by the movement of the second cam 30.

By this method, the first condition and the second condition can be produced by a simple structure without requiring additional components. When the size of the spring 33 falls within the range of the thickness of the first cam 20, the fluid transportation system becomes a thin device having no projection.

Since one cam created by the first cam 20 and the second cam 30 has the finger pressing portions each of which has the same pitch in the circumferential direction and shape, a constant flow amount of fluid can continuously flow during one rotation of the first cam 20 and the second cam 30.

An adjoining pair of the fingers can contact the circumferential area of each finger pressing portion formed on the first cam 20 and the second cam 30, and the condition where an adjoining pair of the fingers among the fingers 40 to 46 close the tube 50 and the condition where one finger closes the tube 50 are alternately repeated. Thus, while the first cam 20 and the second cam 30 rotate the fingers pressed by the finger pressing portions can be sequentially switched. By arranging the structure such that two fingers can contact each finger pressing portion, the tube 50 is constantly closed by one of the fingers being pressed during the period for switching the fingers to be pressed. It is therefore possible to prevent reverse flow of fluid and cause fluid to flow continuously.

In this embodiment, the loading torque of the first cam 20 and the second com 30 (loading torque of cam driving wheel 76) is kept substantially constant during one rotation. Since variation in the loading torque is reduced, the step motor as the driving source for the first cam 20 and the second cam 30 can be made compact and variation in the flow amount of fluid can be reduced.

Since the tube guide portion 123 has the slope for allowing the tube 50 to return to the initial position before closure of the tube 50 at the time of shifting from the closed condition to the released condition of the tube 50, the closed and deformed tube 50 can securely return to the position of the initial condition. Accordingly, the pressed condition of the tube 50 caused by the fingers 40 through 46 can be stabilized, and stable flow of fluid can be maintained.

Moreover, no additional component is necessary to provide this function.

According to the specific example of the fluid transportation system 10 of the invention, a small amount, i.e., 15 μl/hr. of water as fluid is continuously transported when the outside diameter of the tube 50 is 1.1 mm, the diameter of the fluid flow area 51 is 0.6 mm, the rotation number of the first cam 20 and the second cam 30 is 4/hr.

The size of the fluid transportation system 10 is reduced to 18 mm in width, 32 mm in length, and 8.5 mm in thickness.

The invention is not limited to the embodiment described herein. Thus, any modifications, improvements and the like given to the invention within the scope thereof for achieving the object are all involved in the invention.

More specifically, while the specific embodiment according to the invention is chiefly and particularly depicted and described, those skilled in the art can give various modifications to the embodiment described herein with respect to the detailed structure including the shapes, materials, combinations and the like and the processing methods between the manufacturing steps without departing from the technical spirit and object of the invention.

It is therefore intended that the description for limiting the shapes, materials, manufacturing steps and the like disclosed herein are only examples for making the invention easily understood and not at all limit the invention. Any description by component names from which a part or entire limitations to the shapes, materials, combinations and the like are removed is included in the scope of the invention.

For example, while the first cam 20 presses the second cam 30 in the second condition in this embodiment, the second cam 30 may be rotated with the first cam 20 in accordance with the rotation of the cam driving wheel 76 by inserting a shaft formed on the flange 76a of the cam driving wheel 76 into a concave or a hole formed on the second cam 30.

In this structure, the first condition and the second condition can be produced by forming the concave or hole having an oblong shape on a concentric circle around the rotation center P.

Conversely to the this structure, a shaft may be provide on the lower region of the second cam 30 and a concave or a hole may be formed on the flange 76a of the cam driving wheel 76.

INDUSTRIAL APPLICABILITY

The fluid transportation system 10 according to the invention installed inside and outside various types of machinery equipment can transport a fluid such as water, salt water, chemical liquids, oils, aromatic liquids, ink, and gases. In addition, the fluid transportation system can be independently used for flowage and supply of the fluid.

The fluid transportation system is small-sized and can continuously and stably transport a small amount of fluid. Thus, the fluid transportation system is appropriate for medical use such as development of new medicines by attaching the system inside a living body.

The entire disclosure of Japanese Patent Application No: 2005-331451, filed Nov. 16, 2005 is expressly incorporated by reference herein.

What is claimed is:

1. A fluid transportation system, comprising:
   an elastic tube;
   a tube frame having a tube guide groove to which the tube is attached such that the tube forms a circular arc;
   a cam driving wheel disposed inside the tube and having a rotation center coinciding with the center of the circular arc of the tube guide groove;
   a first cam fixed to a center shaft of the cam driving wheel;
   a second cam rotatably supported by the center shaft of the cam driving wheel; and
   a plurality of fingers which radially extend from the rotation center in the space between the tube and the first and second cams and press the tube by the rotation of the first and second cams, wherein:
   when the fluid transportation system starts to operate, the first and second cams produce a first condition in a first state in which the second cam is attached to the first cam and the plural fingers are all released and subsequently produce a second condition in a second state in which the second cam is detached from the first cam and at least one of the plural fingers closes the tube; and
   during operation of the fluid transportation system, the first and second cams sequentially press the plural fingers, and the plural fingers sequentially repeat closure and release of the tube from the inlet side to the outlet side of fluid so that fluid can continuously flow.

2. A fluid transportation system according to claim 1, wherein:
   the second cam is attached to the first cam by an urging force given to the second cam in the thickness direction of the first cam by an elastic member provided on the second cam; and
   removal of the urging force detaches the first and second cams.

3. A fluid transportation system according to claim 1, wherein a condition where two of the fingers close the tube and a condition where one of the fingers closes the tube are alternately repeated.

4. A fluid transportation system according to claim 1, wherein a loading torque of the cam driving wheel is kept substantially constant for one rotation of the cam driving wheel during operation of the fluid transportation system.

5. A fluid transportation system according to claim 1, wherein the tube and the plural fingers can be inserted into the tube frame in the same direction.

6. A fluid transportation system according to claim 1, wherein a tube guide having a slope for returning the tube to an initial position prior to closure of the tube at the time of shifting from the condition where the tube is closed by the fingers to the condition where the closure is released is provided on the bottom of the tube guide groove.

7. A fluid transportation system, comprising:
   an elastic tube;
   a tube frame having a tube guide groove to which the tube is attached such that the tube forms a circular arc;
   a cam driving wheel disposed inside the tube and having a rotation center coinciding with the center of the circular arc of the tube guide groove;

a first cam fixed to a center shaft of the cam driving wheel;

a second cam rotatably supported by the center shaft of the cam driving wheel; and a plurality of fingers which radially extend from the rotation center in the space between the tube and the first and second cams and press the tube by the rotation of the first and second cams, wherein:

when the fluid transportation system starts to operate, the first and second cams produce a first condition in a first state in which the second cam is attached to the first cam and the plural fingers are all released and subsequently produce a second condition in a second state in which the second cam is detached from the first cam and at least one of the plural fingers closes the tube;

when the first and second cams rotate in the first condition and the second cam comes into contact with the finger, the second cam rotates relative to the first cam in the direction opposite to the rotation direction of the first cam around the center shaft of the cam driving wheel by frictional resistance generated on a contact portion between the second cam and the finger, thereby creating the second condition by detaching the first and second cams and pressing the second cam by the first cam; and during operation of the fluid transportation system, the first and second cams sequentially press the plural fingers, and the plural fingers sequentially repeat closure and release of the tube from the inlet side to the outlet side of fluid so that fluid can continuously flow.

8. A fluid transportation system, comprising:

an elastic tube;

a tube frame having a tube guide groove to which the tube is attached such that the tube forms a circular arc;

a cam driving wheel disposed inside the tube and having a rotation center coinciding with the center of the circular arc of the tube guide groove;

a first cam fixed to a center shaft of the cam driving wheel, the first cam having a plurality of finger pressing portions on its outer circumference;

a second cam rotatably supported by the center shaft of the cam driving wheel, the second cam having at least a finger pressing portion on its outer circumference; and a plurality of fingers which radially extend from the rotation center in the space between the tube and the first and second cams and press the tube by the rotation of the first and second cams, wherein:

the plural finger pressing portions formed on the first cam and the finger pressing portion formed on the second cam have the same shape;

an area of each finger pressing portion in the circumferential direction contacts an adjoining pair of the fingers;

when the fluid transportation system starts to operate, the first and second cams produce a first condition in a first state in which the second cam is attached to the first cam and the plural fingers are all released and subsequently produce a second condition in a second state in which the second cam is detached from the first cam and at least one of the plural fingers closes the tube;

the respective finger pressing portions of the first and second cams have the same pitch in the circumferential direction in the second condition; and during operation of the fluid transportation system, the first and second cams sequentially press the plural fingers, and the plural fingers sequentially repeat closure and release of the tube from the inlet side to the outlet side of fluid so that fluid can continuously flow.

* * * * *